United States Patent
Reents, Jr.

[11] Patent Number: 5,977,540
[45] Date of Patent: Nov. 2, 1999

[54] LASER-ASSISTED PARTICLE ANALYSIS

[75] Inventor: William David Reents, Jr., Middlesex, N.J.

[73] Assignee: Lucent Technologies Inc., Murray Hill, N.J.

[21] Appl. No.: 09/061,462

[22] Filed: Apr. 16, 1998

[51] Int. Cl.⁶ .................................................. B01D 59/44
[52] U.S. Cl. ...................................... 250/288; 250/423 P
[58] Field of Search ................................. 250/288, 423 P

[56] References Cited

U.S. PATENT DOCUMENTS

| | | | |
|---|---|---|---|
| 4,584,072 | 4/1986 | Arisawa et al. | 250/423 P |
| 5,382,794 | 1/1995 | Downey et al. | 250/288 |
| 5,631,462 | 5/1997 | Reents, Jr. | 250/288 |

*Primary Examiner*—Kiet T. Nguyen
*Attorney, Agent, or Firm*—Richard J. Botos

[57] ABSTRACT

The present invention provides methods and apparatus for analyzing the particulate contents of a sample such that a high proportion of the sample particles are analyzed without discrimination against high electronegativity and high ionization potential elements. In an exemplary embodiment, the invention comprises an apparatus for analyzing the particulate content of a sample having particulate diameters in the range of 0.001–10 microns. The apparatus comprises an evacuable chamber equipped with a chamber entrance through which a particle-laden gas stream enters. An inlet device, such as a capillary, communicates with the chamber entrance for inputting the particle-laden gas stream to the evacuable chamber. A laser is positioned to produce a focused laser beam which intersect the particle-laden gas stream at position approximately 0.1 mm from the chamber entrance. The laser beam has a power density sufficient to fragment and ionize particles entrained within the particle-laden gas stream. A detector is positioned to detect the ionized species produced by the laser. The laser beam is focused so that the beam has a cross-sectional area in the plane of intersection between the particle-laden gas stream and the laser beam that is at least as large as the cross-sectional area of the particle-laden gas stream in the plane of intersection. In one embodiment, the lens is a set of two cylindrical lenses.

16 Claims, 3 Drawing Sheets

LASER-ASSISTED PARTICLE ANALYSIS

FIELD OF THE INVENTION

The present invention relates to laser-assisted particle analysis and, more particularly, to laser-assisted spectrometry systems for analyzing particulate-laden gas streams.

BACKGROUND OF THE INVENTION

Particle detection and analysis is desirable in a variety of manufacturing and environmental contexts. For example, in clean rooms used for the fabrication of integrated circuits, highly accurate particle detection is required due to the small dimensions of the devices under production. Significant failure rates in integrated circuits are associated with the presence of particles greater than one-tenth the device linewidth. Typically, the smaller the size of the particle, the greater the number of particles which are present. Therefore, as linewidths decrease within the sub-micron range, particle removal becomes increasingly difficult and costly. Consequently, control of a particle source is usually more cost-effective than removal of particles once they are liberated from their source. Through real-time particle analysis, particle sources can be identified and controlled.

Particle detection and analysis in clean rooms and gas distribution systems is typically done by real-time, also known as on-line, counting of airborne particles followed by off-line analysis of deposited particles by microscopic or laser scan techniques. The former technique provides the rapid response required for monitoring particle generation events while the latter technique provides size and elemental composition information. Particle counting is frequently performed using standard light-scattering particle counters. However, these devices can only detect particles and provide no compositional information. While off-line analysis provides particle composition information, it is also limited by the particle sizes it can detect and cannot be time-correlated to particle generation events.

Mass spectrometry is an analytical technique used for the accurate determination of molecular weights, identification of chemical structures, determination of mixture compositions, and quantitative elemental analysis. Molecular structure is typically determined from the fragmentation pattern of ions formed when the molecule is ionized. Element content of molecules is determined from mass values obtained using mass spectrometers. However, since mass spectrometers typically operate in vacuum, particulate analysis usually requires that nearly all of the particular carrier be separated from the particulate material prior to ionization in the spectrometer. This requirement increases the complexity of particle detection for particulates suspended in liquids and gases Laser-induced mass spectrometry is described in U.S. Pat. No. 5,382,794 issued Jan. 17, 1995, commonly assigned to the instant assignee, the disclosure of which is incorporated by reference herein. In the patent, an exemplary laser-induced mass spectrometry system is described in which particles enter an evacuable chamber through an inlet device such as a capillary. A laser, such as a pulsed laser is positioned such that the laser beam intersects the particle stream. As the particles pass through the path of the laser beam, they are fragmented and ionized. A detector, such as a time-of-flight mass spectrometer detects the ionized species. Mass spectra are produced, typically being recorded with an oscilloscope, and analyzed with a microprocessor. The mass spectra information permits real-time analysis of the particle size and composition.

While the laser-assisted spectrometry system described in the patent provides useful real-time particulate analysis, there is a continuing need to provide compositional and size evaluation for increasingly smaller particulates. There is a further need in the art for detection and analysis of a greater percentage of the particulate contents of a sample, to ensure accurate characterization. Finally, there is a need in the art for particulate analysis systems and techniques which do not discriminate against high electronegativity and high ionization potential elements. U.S. Pat. No. 5,361,462, issued May 20, 1997, commonly assigned to the instant assignee, the disclosure of which is incorporated by reference, solves these problems by introducing the particles into the chamber through a capillary tube. A laser is positioned to produce a focused laser beam which intersects the particle laden gas stream at a position approximately 0.05 mm to 1.0 mm from the chamber entrance. The laser beam has a power density sufficient to fragment and ionize particles entrained within the particle-laden gas stream. Although this method and apparatus does not discriminate against high electronegativity and high ionization potential elements, further improvement in the probability of particles being ionized for detection is desired.

SUMMARY OF THE INVENTION

The present invention provides methods and apparatus for analyzing the particulate contents of a sample such that a high proportion of the sample particles are analyzed without discrimination against high electronegativity and high ionization potential elements. In an exemplary embodiment, the invention comprises an apparatus for analyzing the particulate content of a sample having particulate diameters in the range of 0.001–10 microns. The apparatus comprises an evacuable chamber equipped with a chamber equipped with a chamber entrance though which a particle-laden gas stream enters. An inlet device, such as capillary, communicates with the chamber entrance for inputting the particle-laden gas stream to the evacuable chamber. A laser is positioned to produce a focused laser beam which intersects the particle-laden gas stream at a position approximately 0.05 mm to 1.0 mm from the chamber entrance. The laser beam has a power density sufficient to fragment and ionize particles entrained within the particle-laden gas stream. A detector is positioned to detect the ionized species produced by the laser. The laser beam is focused onto an area that is wider than the cross-sectional area of the stream of particles that the laser intersects. This provides greater probability that particles in the beam will be ionized for detection.

In an exemplary embodiment, the capillary dimensions are selected such that the gas flow is less than approximately 2 milliliters/second and the laser beam has a high power density, typically greater than $10^{11} W/cm^2$. These conditions help ensure accurate detection of a large percentage of the particles entrained in a gas stream, typically on the order of 1 in 100 particles.

DETAILED DESCRIPTION

Figure 1:
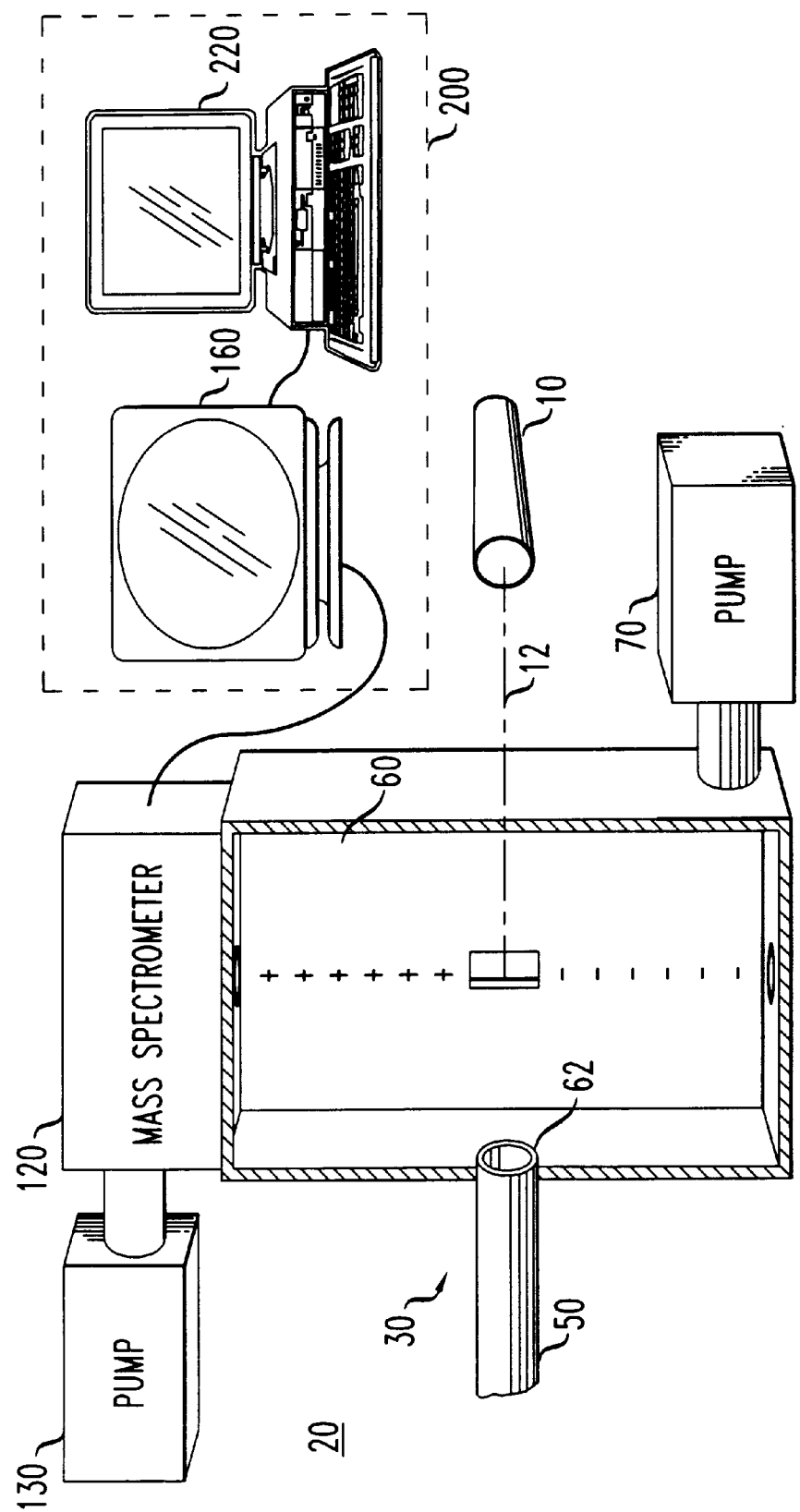
FIG. 1 schematically depicts a laser particle analyzer in partial cross-section according to one embodiment of the present invention.

Referring now to the drawings in detail in which like numerals indicate the same or similar elements in view, FIG. 1 depicts a particle analyzer 20 according to the present invention. The apparatus 20 includes an inlet device 30 through which particles enter a differentially pumped chamber 60. Chamber 60 is generally maintained at a pressure of at least approximately $10^{-3}$ torr by a vacuum pumping system 70. Pumping system 70 is selected from any device capable of maintaining vacuum in the desired range, including, but not limited to, mechanical pumps, diffusion pumps, cryogenic pumps, turbomolecular pumps, and combinations thereof.

Inlet device 30 includes capillary 50 fabricated from materials which provide a smooth interior surface, such as fused silica. Typically, the inner diameter of inlet device 30 is on the order of 0.05 to 0.53 mm with a length of approximately 0.1 to 10 meters for particle analysis in the submicron range. The use of an inlet capillary of these dimensions assists in collimating the particle-laden gas stream and advantageously eliminates the need for mechanical pumping along the path of the capillary. Further, the small capillary size greatly reduces the velocity of the particle-laden gas stream. As a result of the slower gas stream speed, there is a higher probability that a given particle will reside in a laser spot during a laser pulse; resulting in a higher percentage of particles being analyzed. The volume of particle-laden gas flow is typically less than about 2 milliliters/second. The reduced gas stream velocity also reduces the gas load on the pumping system for chamber 60, permitting use of smaller pumping systems or using pumping system 70 for plural pumping functions.

One problem associated with the use of a capillary is that the capillary vibrates or oscillates in response to the vibration of the apparatus. If the cross-sectional area of the laser spot is small, the vibrations and oscillations of the capillary can cause the particle stream to become out of alignment relative to the laser beam. If the particle beam is out of alignment relative to the laser beam, fewer particles are ionized than if the particle beam remained in alignment.

In the method and apparatus of the present invention, a lens that focuses the laser beam in an area of a plane through which the particles are likely to pass is used. In determining the focus area, factors such as capillary vibration, capillary diameter, and distance between the focus area and the capillary outlet are considered.

Figure 2:
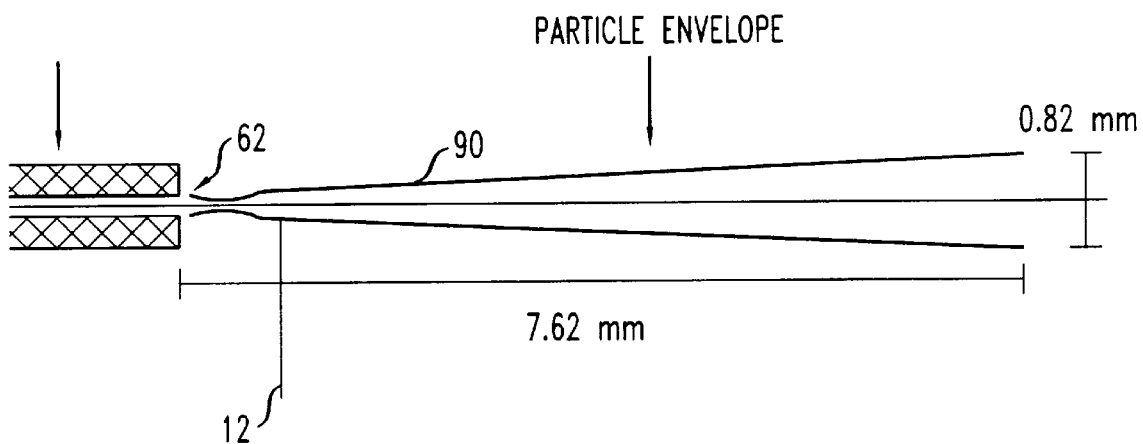
FIG. 2 schematically depicts the particle dispersion from a particle-laden gas stream exiting a capillary and the area of focus for the laser beam using a spherical lens.
Figure 3A:
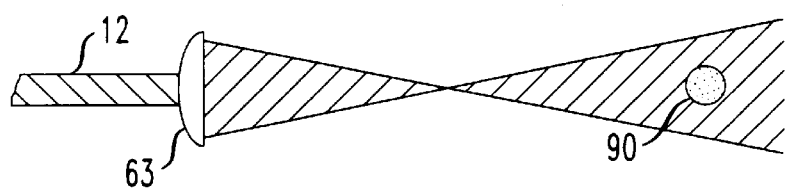
FIG. 3A–3B illustrate one embodiment of the present invention in which a cylindrical lens is used to focus a laser beam in a plane that is horizontal relative to the particle-laden gas stream exiting the capillary.
Figure 3B:
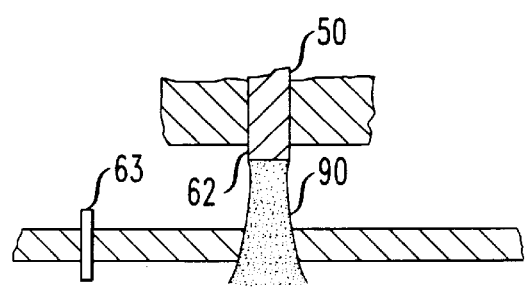
Figure 4A:
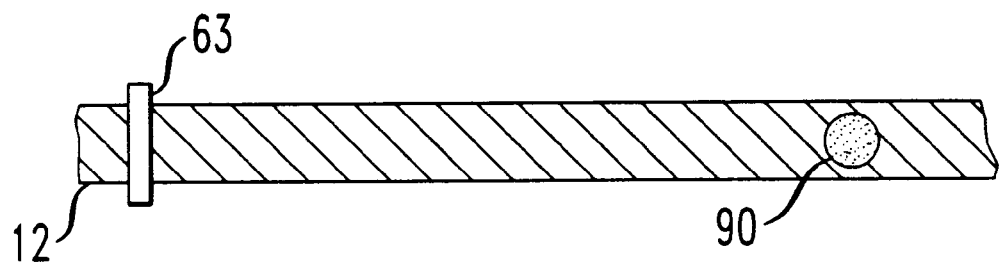
FIG. 4A–4B illustrate one embodiment of the present invention in which a cylindrical lens is used to focus a laser beam in a plane that is vertical relative to the particle-laden gas stream exiting the capillary.
Figure 4B:
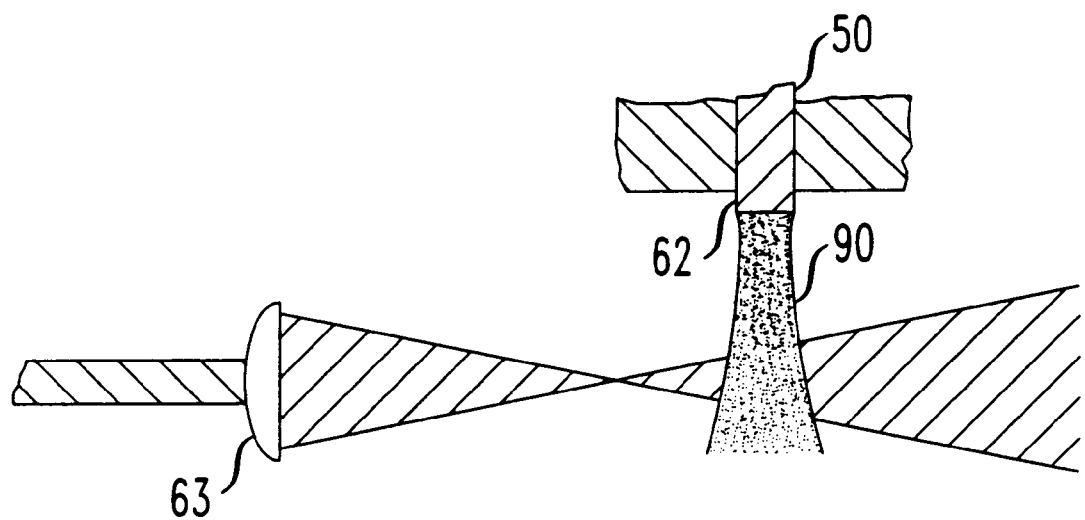

To ionize the particles injected through capillary 50, a laser 10 is positioned such that the focused laser beam passes through an opening in chamber 60 and intersects the particle-laden gas stream adjacent chamber entrance 62. In a preferred embodiment, the edge of the laser beam cross-section at its focus is positioned on the order 0.05–1.0 mm from the chamber entrance. In an exemplary embodiment, the beam edge is positioned 0.1 mm from the chamber entrance. As depicted in FIG. 2, the particle-laden gas stream 90 begins to disperse immediately upon entering chamber 90. As a result of this dispersion, the further away from chamber entrance 62 that the laser beam 12 intersects particle-laden gas stream 90, the smaller is the subtended angle of the dispersion. Further, smaller particles are more easily carried by the expanding gas to a larger radius, while larger particles, e.g., particles greater than one micron, are concentrated in the center of the particle stream. As a result, positioning the focal plane of the laser beam beyond the chamber entrance will tend to discriminate more heavily against analysis of smaller sized particulates. Consequently, a smaller percentage of the total number of particulates is ionized and analyzed for laser/gas stream intersection at any appreciable distance beyond chamber entrance 62. For the described configuration of the FIG. 1 analyzer, approximately 1 out of every 100 particles is analyzed.

As illustrated in FIG. 2, the laser beam 12 intersects the particle-laden gas stream 90 a certain distance from the chamber entrance 62. FIG. 2 does not depict the focus of the laser beam, and is provided as a schematic illustration of the intersection of the laser beam and the particle-laden gas stream.

In the present invention the laser beam is transmitted through a lens that focuses the laser beam such that the laser beam has a cross sectional area in a plane that intersects the particle beam that is at least as large as the cross-sectional area of the particle-laden gas stream at the point of intersection. This is illustrated in FIG. 3A, which is a view in a plane that intersects particle laden gas stream 90. In the embodiment illustrated in FIG. 3A, a cylindrical lens 63 is used to focus the laser beam 12. In a cylindrical lens, the laser beam focuses in the horizontal plane (FIG. 3A) and not in the vertical plane (FIG. 3B). Thus, the lens depicted in FIG. 3A and 3B does not focus the laser beam in the vertical plane. However, in a cylindrical lens, a second lens focuses the laser beam in the vertical plane but not the horizontal plane (the opposite of the situation depicted in FIGS. 3A and 3B) as illustrated in FIG. 4 A–B. For reference, since horizontal and vertical are relative terms, the horizontal plane is the plane substantially perpendicular to the capillary opening. The vertical plane is the plane relatively parallel to the capillary opening.

One example of a suitable cylindrical lens is a fused silica lens that is transparent to radiation at a wavelength of 532 nm (the wavelength of the Spectra Physics DCR II laser described below). For the two cylindrical lenses, the first lens has a focal length of 100 mm and the second lens has a second focal length of 300 mm. Such a combination of lenses is commercially available from Newport, of Irvine, Calif. The focal lengths described above are just examples. One skilled in the art will appreciate that other lens combinations having focal lengths other than the focal lengths specified above will be suitable for use in the present invention.

A spherical lens is also contemplated as suitable for use in the present invention. In a spherical lens, the focus in the horizontal and vertical planes is the same. However, the focus of a spherical lens is adjustable to provide a focused laser beam that has an area cross section in the plane of intersection with the particle-laden gas stream that is at least about the same as the cross section of the particle-laden gas stream at the plane of intersection. However, if a spherical lens is used in the process of the present invention, the focal length of the lens is required to be about 200 mm or less in order for the laser beam to have the power density required by the process.

In the process of the present invention, the amount of focal length adjustment is limited by the power density requirement for the laser beam when it intersects the particle-laden gas stream. In the embodiment of the present invention wherein the lens is a spherical lens, it is noted that there is a smaller window of adjustment available than in the embodiment wherein the lens is a set of two cylindrical lenses.

In one embodiment, the desired spatial relationship among capillary 50, chamber entrance 62, and laser beam 12, is created through use of a precision x-y-z manipulator (not shown). It is emphasized that use of an x-y-z manipulator is illustrative. Any arrangement, adjustable, or fixed, which ensures the proper spatial relationship among these components can be used with the particle analyzers of the present invention. Capillary 50 is positioned within the manipulator and set to the desired distance from the laser beam. In a further embodiment, the position of the lens is also adjustable, thereby providing for more degrees of adjustment. Using these adjustments, a laser beam with both the requisite cross-section in the plane of intersection with the particle laden gas stream and the requisite power density is provided.

The vibrations of the capillary cause the capillary opening to move relative to the focus of the laser beam. Consequently, these vibrations move the exiting particle stream relative to the focus of the laser beam. In the present invention, a lens system that provides a wider focus for the laser beam is used to provide a broader region of overlap between the particle stream exiting from the vibrating capillary tube and the focus of the laser beam.

Laser 10 is selected from pulsed lasers having a short pulse width, a high peak power, a moderate spot size, and a high repetition rate. For the embodiment shown in FIG. 1, laser 10 has a pulse frequency in the range of 10 Hz to 100 kHz with a frequency of from 1 to 10 kHz being exemplary. The laser power is at least approximately 10 mJ with a power density on the order of at least $1.0 \times 10^{10}$ W/cm$^2$ with power densities of greater than $1.0 \times 10^{12}$ W/cm$^2$, and, more particularly, greater than $1.0 \times 10^{13}$ W/cm$^2$, being exemplary. Laser spot sizes are determined by the selected laser power and power density. Typically, laser spot sizes range between 0.003 to 0.1 mm$^2$.

The use of high laser power densities ensures the ability to fully characterize the particle-laden gas stream. High laser power densities ensure ionization of high ionization potential elements. Additionally, smaller particles, which are more difficult to ionize since they transfer heat more efficiently than larger particles, ionize more readily at the higher laser power densities used in the present invention. Acceptable commercially-available lasers include a Lambda Physik excimer laser, model EMG 202, and a Spectra Physics DCR II Neodymium YAG laser.

Upon introduction of the particle-laden gas stream 90 into capillary 50, laser 10 is turned on and continuously fired. As the particle-laden gas stream enters chamber 60, it passes through the laser beam. The laser beam fragments a particle and ionizes the fragments, forming a plasma. For the high power densities of the present invention, the particle fragments yield positive ions.

A time-of-flight mass spectrometer (TOF/MS) 120, particularly a time-of-flight mass spectrometer including a reflectron, obtains the mass spectra provided by particles ionized by laser 10. While a time-of-flight mass spectrometer is depicted in FIG. 1, it is understood that this spectrometer is illustrative. A variety of mass spectrometers can be employed in the particle analyzers of the present invention including, but not limited to, quadrapole, magnetic, sector, and quadrapole ion trap spectrometers, and Penning ion trap spectrometers such as FTICR spectrometers. Time-of-flight mass spectrometer 120 is a positive time-of-flight mass spectrometer. Pump system communicates with the spectrometer to maintain a pressure of less than approximately 10$^{-4}$ torr. Optionally, pump system 130 is combined with pump system 70 through a plural port system, reducing the number of pumping elements and hence the overall size and cost of the system.

Due to the high laser power densities employed in the present invention, the ionized particle fragments in the plasma are positive species. The spectrometer counts each fragmentation incident and measures the masses and yields of the positive ions produced when the particle contacts the laser beam. The mass of the ions correlates to the travel time required for the ionized particle fragment to contact the mass spectrometer. A Jordan Associates dual time-of-flight mass spectrometer can be employed as spectrometer 12. Optionally, a positively charged grid (not shown) is positioned opposite spectrometer 120 to accelerate the positively charged ions toward the spectrometer.

Information from the spectrometer is transmitted to recording portion 200. In an exemplary embodiment, recording portion comprises a transient recorder 160, such as a digital oscilloscope, which records the mass spectra. Processor 220, such as a computer, analyzes and displays the information received from oscilloscope 160. Optionally, the processor itself included in recorder 160. It is understood that recording portion 200 is exemplary and that any device capable of recording, displaying, or otherwise processing information from spectrometer 120 is employable as element 200.

The apparatus and methods of the present invention are able to detect very small particles, such as those with a diameter of less than 0.03 micron. These very small particles produce a small number of ions. This small number results in a low ion density which reduces ion spreading during their flight time. Reduced ion spreading significantly contributes to an increase in the mass resolution of the time-of-flight mass spectrometer. The mass resolution relates to the width of the arrival time of ions with the same mass. Also, particle fragmentation and ionization time must be short; high laser power densities facilitate particle fragmentation and ionization in time periods less than the laser pulse width.

Ions from these very small particles produce pulse widths of less than 2 nanoseconds. For the above-described system, an ultrahigh mass resolution of greater than 30,000 at ion mass 180 is achieved. Currently, such resolutions are attained only by massive, costly, magnet-based mass spectrometers. The ability to achieve these resolutions with time-of-flight mass spectrometers represents a considerable cost and size reduction over prior art systems.

Advantageously, the laser-assisted particle analyzers of the present invention substantially completely fragment and ionize the incident particles due to high laser power density. In contrast, low power densities do not completely ionize fragments, so complete particle information is not obtained. By completely fragmenting and ionizing an incident particle, the ionized fragments yield an accurate representation of the parent particle. Consequently, ion measurements yield the amount of particular elements in the particle and the mass of material present in the particle can be directly determined from ion intensities. Other particle techniques typically determine a particle diameter and assume an ideal spherical shape. Mass is derived from the assumed shape using an estimated density. This approximation is especially poor for irregularly-shaped particles and those particles which are porous.

The present invention permits real-time detection and analysis of particles. Real-time analysis is particularly useful for evaluation of particles whose existence is transitory. For example, mechanical devices, when moved, generate a burst of particles for only a short time. Gas transport through a conduit can cause particles to be shed from inner surfaces, especially during pressure changes. Evaluating the composition of these particles, especially those smaller than 0.1 micron in diameter, is made possible through the apparatus and techniques of the present invention. Additionally the present invention is useful for the analysis of the particulate contents of liquid samples.

While foregoing invention has been described in terms of the exemplary embodiments, it will be readily apparent that numerous modifications such as those suggested above, but not limited thereto, are considered to be within the scope of the claimed invention.

What is claimed is:

1. Apparatus for analyzing the particulate content of a sample, the sample particulates having a diameter in a range of 0.001–10 microns, the apparatus comprising:

an evacuable chamber, the evacuable chamber including a chamber entrance through which a particle-laden gas stream enters;

an inlet device communicating with the chamber entrance for inputting the particle-laden gas stream to the evacuable chamber at a velocity of less than about 64 m/sec.;

a laser positioned to produce a laser beam focused in a plane which intersects the particle-laden gas stream at a position of 0.1 mm from the chamber entrance wherein the focused laser beam has a cross-sectional area that is at least as large as the cross-sectional area of the particle-laden gas stream in a plane of intersection between the focused laser beam and the particle-laden gas stream, the laser beam having a power density, in the plane of intersection sufficient to fragment and ionize particles entrained with the particle-laden gas stream; and a detector positioned to detect ionized species produced by the laser.

2. The apparatus of claim 1 further comprising a lens to focus the laser beam wherein the lens is selected from the group consisting of a spherical lens and a pair of cylindrical lenses.

3. Apparatus for analyzing the particulate content of a sample according to claim 2 wherein the inlet device is a small diameter capillary.

4. Apparatus for analyzing the particulate content of a sample according to claim 3 wherein the small diameter capillary has a diameter of approximately 0.05–0.53 mm and a length on the order of 0.1–10 meters.

5. Apparatus for analyzing the particulate content of a sample according to claim 2 further comprising a precision x-y-z manipulator supporting either the capillary, the lens or both, for maintaining the focused laser beam at a position approximately 0.1 mm from the chamber entrance.

6. Apparatus for analyzing the particulate content of a sample according to claim 2 wherein the laser has a power density of at least $10^{10}$ W/cm$^2$.

7. Apparatus for analyzing the particulate content of a sample according to claim 2 wherein the laser has a power density of at least $10^{12}$ W/cm$^2$.

8. Apparatus for analyzing the particulate content of a sample according to claim 2 wherein the laser has a power density of at least $10^{13}$ W/cm$^2$.

9. Apparatus for analyzing the particulate content of a sample according to claim 2 wherein the detector comprises a mass spectrometer.

10. Apparatus for analyzing the particulate content of a sample according to claim 9 wherein the mass spectrometer comprises a time-of-flight spectrometer.

11. A method for analyzing the particulate content of a sample, the sample particulates having a diameter in a range of 0.001–10 microns, the method comprising:

inputting a particle-laden gas stream through an inlet device at a velocity of less than about 64 m/sec. into an evacuable chamber through a chamber entrance;

focusing a high power density laser in a plane to produce a focused laser beam with a cross-sectional which intersects the particle-laden gas stream at a position approximately 0.1 mm from the chamber entrance wherein the cross-sectional area of the laser beam is at least as large as the cross-sectional area of the particle-laden gas stream in the plane of intersection of the laser beam and the particle-laden gas stream, the laser beam having a power density sufficient to fragment and ionize particles entrained within the particle-laden gas stream;

fragmenting and ionizing particles entrained within the particle-laden gas stream; and detecting ionized species produced by the laser interaction with the particle-laden gas stream.

12. The method of claim 11 wherein a lens is used to focus the laser beam wherein the lens is selected from the group consisting of a spherical lens and a set of two cylindrical lenses.

13. A method for analyzing the particulate content of a sample according to claim 11 wherein the detecting is performed using a time-of-flight mass spectrometer.

14. A method for analyzing the particulate content of a sample according to claim 11 wherein the inlet device comprises a capillary.

15. A method for analyzing the particulate content of a sample according to claim 11 wherein the laser has a power density of at least $10^{10}$ W/cm$^2$.

16. A method for analyzing the particulate content of a sample, the sample particulates having a diameter in a range of 0.001–10 microns, the method comprising:

inputting a particle-laden gas stream through an inlet device into an evacuable chamber at a velocity of less than about 64 m/sec. through a chamber entrance;

focusing a high power density laser in a plane to produce a focused laser beam which intersects the particle-laden gas stream in the evacuable chamber wherein the focused particle beam has a cross-sectional area that is at least as large as the cross-sectional area of the particle-laden gas stream in the plane of intersection of the laser beam and the particle-laden gas stream, the laser beam having a power density sufficient to fragment and ionize particles entrained within the particle-laden gas stream wherein the laser beam is focused using a lens and wherein the lens is selected from the group consisting of a spherical lens and a cylindrical lens;

substantially completely fragmenting and ionizing incident particles from the particle-laden gas stream; and detecting ionized species produced by the laser interaction with the particle-laden gas stream to directly yield mass and/or compositional data about a particle.

\* \* \* \* \*